US009273087B2

(12) United States Patent
Rothstein et al.

(10) Patent No.: US 9,273,087 B2
(45) Date of Patent: Mar. 1, 2016

(54) HYBRID SOLID SUPPORTS USEFUL FOR OLIGONUCLEOTIDE PRODUCTION

(71) Applicant: PRIME SYNTHESIS, INC., Aston, PA (US)

(72) Inventors: Marc L. Rothstein, Ambler, PA (US); Dianne M. Rothstein, Ambler, PA (US); Dan P. Lee, Reno, NV (US)

(73) Assignee: Prime Synthesis, Inc., Aston, PA (US)

( * ) Notice: Subject to any disclaimer, the term of this patent is extended or adjusted under 35 U.S.C. 154(b) by 0 days.

(21) Appl. No.: 14/599,787

(22) Filed: Jan. 19, 2015

(65) Prior Publication Data

US 2015/0133648 A1 May 14, 2015

Related U.S. Application Data

(60) Division of application No. 14/096,081, filed on Dec. 4, 2013, now Pat. No. 8,956,725, which is a continuation of application No. 12/145,051, filed on Jun. 24, 2008, now Pat. No. 8,628,822.

(60) Provisional application No. 60/986,639, filed on Nov. 9, 2007, provisional application No. 60/937,611, filed on Jun. 28, 2007.

(51) Int. Cl.
*C07H 21/00* (2006.01)
*C03C 17/32* (2006.01)
*C03C 11/00* (2006.01)
*G01N 33/543* (2006.01)
*G01N 33/552* (2006.01)

(52) U.S. Cl.
CPC .............. *C07H 21/00* (2013.01); *C03C 11/00* (2013.01); *C03C 17/32* (2013.01); *C03C 17/328* (2013.01); *G01N 33/54313* (2013.01); *G01N 33/54353* (2013.01); *G01N 33/552* (2013.01); *Y10T 428/2989* (2015.01); *Y10T 428/2996* (2015.01); *Y10T 428/2998* (2015.01)

(58) Field of Classification Search
CPC ....................................................... C07H 21/00
See application file for complete search history.

(56) References Cited

U.S. PATENT DOCUMENTS

| | | | |
|---|---|---|---|
| 4,029,583 A | 6/1977 | Ho Chang et al. |
| 4,140,653 A | 2/1979 | Imura et al. |
| 4,632,108 A | 12/1986 | Geil |
| 4,663,880 A | 5/1987 | Grobl |
| 4,732,887 A | 3/1988 | Obanawa et al. |
| 4,746,572 A | 5/1988 | Glajch |
| 4,847,159 A | 7/1989 | Glajch |
| 5,049,374 A | 9/1991 | Danscreau et al. |
| 5,114,577 A | 5/1992 | Kusano et al. |
| 5,141,813 A | 8/1992 | Nelson |
| 5,633,081 A | 5/1997 | Clough et al. |
| 5,872,207 A | 2/1999 | Morgan et al. |
| 5,958,310 A | 9/1999 | Pauls |
| 6,028,189 A | 2/2000 | Blanchard |
| 6,228,937 B1 | 5/2001 | Eck et al. |
| 6,307,042 B1 | 10/2001 | Goldberg et al. |
| 6,355,429 B1 | 3/2002 | Nygren et al. |
| 6,808,908 B2 | 10/2004 | Yao et al. |
| 8,129,517 B1 | 3/2012 | Letuchy et al. |
| 2007/0135626 A1 | 6/2007 | Ngo et al. |
| 2007/0287832 A1 | 12/2007 | Gao et al. |
| 2008/0264867 A1 | 10/2008 | Mika et al. |
| 2009/0005536 A1 | 1/2009 | Rothstein et al. |

FOREIGN PATENT DOCUMENTS

| | | |
|---|---|---|
| ES | 8701823 A3 | 3/1987 |
| GB | 2316021 A | 2/1998 |
| WO | WO97/27150 A1 | 7/1997 |

OTHER PUBLICATIONS

Wisniewska et al, The Tempature Influence on the Adsorption and Electrokinetical Properties in the Nonionic Polymer/Controlled Porosity Glass (CPG) System, ScienceDirect, Materieals Chemistry and Physics, vol. 103, pp. 216-221, (May 2007).
Janowski, "Poröse Gläser, Herstellung, Eigenschaften und Anwendung" VEB Deutscher Verlag Fur Grundstoffingustrie, Leipzig, pp. 152-198, (1982), Item XP-002506347.
Camps et al, Chloromethylstyrene: Synthesis, Polymerization, Transformations, Applications, Journal of Macromolecular Science, Reviews in Macromolecular Chemistry and Physics, vol. C22, pp. 343-407, (1982).
Elmer, TH, "Porous and Reconstructed Glasses", Engineered Materials Handbook, vol. 4, Ceramic and Glasses, p. 427-32 (1992).
Lloyd, Nucleophilic displacements upon poly(vinylbenzyl chloride), Journal of applied polymer science, vol. 7, p. 2025-2033 (1963).
Takeuchi, Solid dispersion particles of amorphous indomethacin with fine porous silica particles by using spray-drying method, International Journal of Pharmaceutics 293 (Apr. 11, 2005), p. 155-164.
Metwalli, Surface characterization of mono, di, and tri aminosilane treated glass substrates, Journal of Colloid and Interface Science 298 (Jun. 15, 2006; epub Mar. 27, 2006), p. 825-831.
Rothstein et al, A New High Efficiency Hybrid Solid Support for Oligonucleotide Synthesis, Prime Synthesis, May 2011.
Rothstein et al, Evaluation of a Hybrid CPG Soil Support for Oligonucleotide Synthesis, Prime Synthesis, May 2012.
Rothstein et al, Solid-Phase Supports for Oligo Synthesis, Genetic Engineering and Biotechnology News, May 2012, vol. 32, No. 9.

(Continued)

*Primary Examiner* — Jonathan S Lau
(74) *Attorney, Agent, or Firm* — Howson and Howson LLP

(57) ABSTRACT

A method for preparing a crosslinked polymer coated controlled porosity glass (CPG) particle is provided. The method involves mixing CPG particles in a solution comprising polyvinylbenzylchloride and a first solvent at a temperature below 10° C. A second solvent is added and a crosslinking agent is added to the mixture. The first solvent is removed rapidly within 1½ hours of addition of the crosslinking agent. The crosslinking reaction is permitted to proceed and the mixture is then cooled and treated to remove any remaining solvent. The resulting coated CPG particles are washed and dried. Also provided a polymer coated CPG particles using for loading ligand thereon.

18 Claims, No Drawings

(56) References Cited

OTHER PUBLICATIONS

Brown, Tom, et al, "Solid-Phase Supports for Oligo Synthesis", http://www.atdbio.com/content/17/Solid-phase-oligonucleotide Synhttp://www.atdbio.com/content/17/Solid-phase-oligonucleotide-synthesis, part of Nucleic Acid Book, ATDBio. 2005-2012.
OPPT Chemical Fact Sheet, 1,4-dioxane, p. 1-2, Feb. 1995.
European Patent Application No. 08779740.3-1218 of Aug. 11, 2011, Communication pursuant to Article 94(3).
Response dated Dec. 21, 2011 to the Communication (exam report) dated Aug. 11, 2011 issued in EP 08779740.3.
International Preliminary Report on Patentability for PCT/US2008/007840, issued Jan. 5, 2010, in the counterpart PCT application.
Office Action dated Sep. 23, 2011 in U.S. Appl. No. 12/145,051.
Response to Office Action, dated Oct. 24, 2011 in U.S. Appl. No. 12/145,051.
Non-Final Rejection dated Dec. 8, 2011 in U.S. Appl. No. 12/145,051.
Response to Non-Final Rejection, dated Mar. 8, 2012 in U.S. Appl. No. 12/145,051.
Non-Final Rejection dated Jun. 8, 2012 in U.S. Appl. No. 12/145,051.
Response to Non-Final Rejection, dated Oct. 9, 2012 in U.S. Appl. No. 12/145,051.
Final Rejection dated Feb. 4, 2013 in U.S. Appl. No. 12/145,051.
Response to Final Rejection, dated May 1, 2013 in U.S. Appl. No. 12/145,051 and Rule 132 Declaration.
Advisory Action Before Filing of an Appeal Brief dated Jun. 10, 2013 in U.S. Appl. No. 12/145,051.

HYBRID SOLID SUPPORTS USEFUL FOR OLIGONUCLEOTIDE PRODUCTION

CROSS-REFERENCE TO RELATED APPLICATIONS

This application is a divisional application of U.S. patent application Ser. No. 14/096,081, filed Dec. 4, 2013, which is a continuation pursuant to 35 USC 120 of U.S. patent application Ser. No. 12/145,051, filed Jun. 24, 2008, now U.S. Pat. No. 8,628,228, which claims the benefit under 35 USC 119(e) of U.S. Provisional Patent Application No. 60/986,639, filed Nov. 9, 2007 and U.S. Provisional Patent Application No. 60/937,611 filed Jun. 28, 2007. These applications are hereby incorporated by reference.

BACKGROUND OF THE INVENTION

The invention relates generally to solid supports for solid phase chemical synthesis.

The use of a variety of solid supports has been described for use in the synthesis of oligonucleotides.

Currently, controlled porosity glass (CPG) particles are used in large-scale oligonucleotide synthesis. However, these particles have limited capacities for loading and length of the nucleoside. More particularly, chemical loading levels for glass are limited to "native" silanol concentrations on the surface of the glass. For glass, there is a fixed quantity of silanol groups per unit surface area. The surface area is inversely proportional to the pore size. Thus, even though high pore sizes are favorable from a synthesis point of view, such CPG's have a low loading capacity compared to a polymeric support.

Thus, polymeric supports have been used for oligonucleoside synthesis, including, e.g., polystyrene-based particles. The use of low crosslinked polystyrene particles has been described for polypeptide synthesis. These do not accommodate high-yield oligonucleotide synthesis, due to their high degree of swelling in the synthesis solvents. Highly crosslinked particles have been used for large scale synthesis. Although this type of solid support swells much less, it has a limited nucleoside loading capability and is compressible.

In order to address these problems, polystyrene of intermediate crosslinking has been used to achieve higher loading capacities. These supports do swell considerably, and therefore, overall volumetric yield is compromised. Furthermore, compressibility is greater than that of the higher crosslinked polystyrene.

What are needed are additional solid supports for solid phase synthesis.

SUMMARY OF THE INVENTION

The invention provides a coated particle for solid phase chemical synthesis having a core and a conformal polymeric coating over said core.

Suitably, the core is a controlled porosity glass which provides the particle of the invention with mechanical stability, thereby avoiding the significant compression problem associated with polystyrene beads. The conformal polymeric coating provides the coated particle with a limited ability to swell, thereby providing higher loading capacities than traditional solid silica based supports and more effective nucleoside attachment sites.

In another aspect, the invention provides a method for preparing a crosslinked polymer coated controlled porosity glass (CPG) particle. The method comprises mixing CPG particles in a solution comprising polymer and a first solvent at a temperature below 10° C. A second solvent is added and a crosslinking agent is added to the mixture. The first solvent is removed rapidly within 1½ hours of addition of the crosslinking agent. The crosslinking reaction is permitted to proceed and the mixture is then cooled and treated to remove any remaining solvent. The resulting coated CPG particles are washed and dried. In one embodiment, the resulting coated CPG particle is characterized by having a pore size and total pore volume within 90% of the pore size (based on dry or unsolvated state) and total pore volume of the CPG substrate.

In another aspect, the invention further provides a vessel for solid phase chemical synthesis which vessel comprises a plurality of coated particles of the invention.

In yet another aspect, the invention provides a method for solid phase synthesis of a ligand which comprises synthesizing the oligonucleotides on a coated particle.

Other aspects and advantages of the invention will be readily apparent from the following detailed description of the invention.

DETAILED DESCRIPTION OF THE INVENTION

The invention provides a novel method for coating controlled porosity glass (CPG) surfaces to provide a polymer coated CPG particle useful for solid phase chemical synthesis. The resulting polymer coated CPG particle of the invention provides the advantages of rigidity and pore structure/solution transmission characteristics and overcomes the limiting loading capacity of native CPG.

Controlled porosity glass (CPG) substrates may be obtained from a variety of commercial sources including, e.g., Prime Synthesis, Inc. and Millipore. Corp. In one embodiment, the CPG substrates are particles and may be irregularly shaped. These particles may be in the range of about 10 to 500 microns, about 25 to 300 microns, about 75 to 125 microns. However, larger or smaller particles may be selected by one of skill in the art.

Suitably, the CPG substrate contains pores with a mean average diameter of 75 to 4000 Angstroms, a mean average diameter of 100 to 500 to 3000 Angstrom, a mean average diameter of at least 1000 to 2500 Angstroms, a mean average diameter of 600 Angstroms to 900 Angstroms, or 700 Angstroms to 800 Angstroms. In another embodiment, the CPG substrate contains pores of a larger or smaller mean average diameter.

The invention provides a CPG substrate with a polymeric coating which swells without significantly reducing pore size. Reactive amino groups in the polymerized coating provide increased loading capacity as compared to native CPG. The polymeric coating is layered on the surface of the CPG substrate and is completely conformal, in that it coats the pores but does not block them. Advantageously, the method of the invention permits the polymeric coating to be deposited directly on the CPG without requiring the use of a silane coupling agent or an intermediate coat. For example, in one embodiment, a coated CPG substrate has an average pore size of at least about 90% of the average pore size of the uncoated substrate (based on dry pore size). In another embodiment, a coated CPG substrate of the invention has an average pore size of at least about 95%, at least about 97%, at least about 98%, at least about 99%, of the average pore size of the uncoated substrate (based on dry CPG).

The term "conformal coating" refers to a coating which is a layer that is located within the pores of the surfaces of the CPG substrate and which does not change the shape of the article formed by substrate.

The polymeric material selected for the outer coating in the article of the invention is a material which contains functionalized groups useful for loading molecules for synthesis. In one embodiment, the functional groups are present at the time the outer coating is deposited on the core. However, the functional groups may be provided to the outer coating following deposit.

Thus, the polymeric coating is provided with functional groups such as, e.g., aldehydes, amino groups, epoxy, halides, carboxylic acid, esters, or mixtures thereof. Methods of providing these functional groups to the polymeric material are known to those of skill in the art. In one embodiment, the invention provides a coated particle having amino functional groups for use in oligonucleotide synthesis and other applications.

In one embodiment, the polymeric material is a polystyrene or a poly(vinyl), such as poly(vinylbenzylchloride). In still another embodiment, the polymeric coating can be prepared from a polymerizable monomer, e.g., an acrylic, a polystyrene (neutral and functionalized), polyethylene glycol or polyvinyl alcohol, which is polymerized during or prior to the coating.

As used herein, the terms "styrene" and "vinylbenzene" are interchangeable. In one embodiment, the outer coating is a polystyrene. For example, the polystyrene can be selected from among polystyrenes having high, low or medium cross-linking. The degree of cross-linking of the polymer can range from 2% to 40% cross-linking agent, preferably about 5 to 30%.

In one embodiment, a cross-linked polystyrene is prepared from a mixture of a styrene copolymer such as styrene monomer and divinyl benzene, and benzoyl peroxide, which is the cross-linking agent. Practical embodiments of the invention have been produced using these components to modify the density. Both of these components have densities which are less than 1.02 g/cc.

Cross-linked polystyrene can be prepared using methods which are well known to those of skill in the art. For example, for polymerization, a ratio of divinyl benzene (DVB) to styrene monomers may be in the ratio of about 1 weight percent DVB to about 100 weight % styrene monomers. However, other suitable ratios within this range may be readily selected by one of skill in the art including, e.g., 1 wt % to 60 wt %, or 1 wt % to 45 wt %. In one embodiment, the ratio of DVB to styrene about 1 to about 8 weight %. Based on the total monomer(s) added for the polymerization, a diluent or solvent for the monomers is added at a weight ratio percent of about 1 to about 200, about 5% to about 150%, about 10% to about 100%, about 20% to about 75%, about 25% to about 50%, by weight of solvent/diluent to the weight of monomer(s).

In one embodiment, a methacrylate monomer, e.g., an alkyl methyacrylate such as methyl methacrylate, is used to form the coating material. For example, other suitable monomers useful for forming the outer coating layer are vinyl monomers such as styrenes, acrylates, methacrylates and the like. Derivatives of these alkyl methacrylate monomers, for example, methyl acrylate, butyl acrylate, methyl methacrylate, and functionalized derivatives, for example, bromo styrene, chloromethyl styrene, 2-aminoethyl methacrylate, and trimethylammoniumethyl methacrylate, may also be used. Cross-linked polystyrene may be purchased commercially from, e.g., GE Healthcare and Nitto Denko. Inclusion of a desired percentage of functionalized derivatives eliminates the step of providing functionalized groups after the polymerization has been completed. When the monomer chosen to be added in the dispersed phase has only one vinyl group, it is desirable to include another monomer having more than one vinyl group to facilitate cross-linking. In one embodiment, the ratio of various monomers is chosen to provide a final polymer crosslinked to the extent of about 5 to 30%. In yet another embodiment, the coating can be a polyamide.

The coating is desirably provided in a thin uniform layer over the CPG particle. In one embodiment, the coating is present in an about amount of about 2% w/w to about 15% w/w, and more desirably, about 5% to about 10%, of the total weight of the coated particle. In one desirable embodiment, a poly(vinylbenzylchloride) coating is present in an amount of about 6% w/w of the total weight of the coated particle. For example, the polymeric coating may have a thickness in the range of about 20 Angstroms to about 100 Angstroms.

Desirably, the polymer forming the coating is crosslinked in the range of from 2% to 40%. The use of low (about 2% to about 14% crosslinking), medium (about 15% to about 25% crosslinking), or high cross-linking (about 30 to 40% crosslinking) can be readily determined by one of skill in the art taking into consideration the selected polymer. For example, about 5% to about 30% crosslinking is desirable for poly(vinylbenzylchloride) polymers.

In one embodiment, a crosslinking agent is used to facilitate crosslinking in the polymeric coating. Suitable crosslinking agents can be readily selected from among difunctional compounds whose functional groups react with a group in the monomeric subunits of the polymer. For example, the crosslinking agent reacts with the benzylchloride moiety of the vinylbenzylchloride monomer. The functional groups of the crosslinking agent can include, but are not limited to, amines, thiols, diols, bisphenols, diphosphines, sulfonates, epoxides, nitriles, carboxylates, arylhalides, aldehydes, acetates, and thioesters (e.g, carboxylic thioesters), phosphate esters.

In one embodiment, the crosslinking agent is a diaminobutane (DAB). In one example, 1,4-diaminobutane is used. However, other crosslinking agents may be readily selected.

In another embodiment, a poly(vinylbenzylchloride) (poly (VBC)) can be crosslinked through other methods known to one of skill in the art including, e.g., using Friedel-Crafts catalysts including, but not limited to $AlCl_3$. Advantageously, the method of the invention avoids the need for a coupling agent to link the coating to the silane substrate of the glass particle.

Although less desirable, the method of the invention could be used with such an agent. An exemplary silane coupling agent has a formula [—$Si(CH_2)_n$]—R, wherein n is 1, 2, 3, 4, 5 or 6, and R is a moiety selected to react with the monomer or polymeric coating. The Si group may be provided as part of the linker. Thus, the linkage may be provided by a modification to the surface of the glass substrate. In another embodiment, the linkage may be provided by a modification to the polymer which forms the outer coating.

In one aspect, the invention provides a method for providing a polymer-coating to a controlled porosity glass (CPG) particle, which polymer coating is stable during reaction to provide the desired functional groups (where reaction following deposit of the coating is required) and is stable during loading, e.g., with a desired ligand. Preferably, the polymer-coated CPG of the invention retains the pore volume and at least about 90% of the pore size of the CPG substrate in the dry (unsolvated) state. It will be readily understood by one of skill in the art that in the solvated state, the pores of the polymer coated CPG are about 20-50% filled with the coating.

Thus, in one aspect, the invention provides a process for coating a controlled porosity glass (CPG) particle with a crosslinked polymer. The process involves the steps of mixing the CPG particles with the desired monomer or polymer which will form the polymeric coating. The CPG particles and the solution are cooled to a temperature below about 10° C., e.g., about −20° C. to about 10° C., preferably about 0° C. to about 5° C. The CPG particles and/or the solution can be cooled prior to mixing.

The solution contains the selected monomer(s) or the polymer and a solvent which will dissolve the polymer (or monomer) and cross-linking agent. Desirably, the dissolution is at a level such that the solution will fit within the volume of the pores of the CPG particle. Examples of suitable solvents include, e.g., dichloromethane (also termed methylene chloride) (DCM), tetrahydrofuran, 2-MeTHF, methyl ethyl ketone (MEK), ethyl acetate, benzene, butyraldehyde, chloroform and acetone. Other suitable solvents can be readily selected by one of skill in the art.

In one embodiment, the solution contains polyvinylbenzylchloride and DCM. In one particularly desirable embodiment, a sufficient amount of polyVBC is provided to allow the dispersion of the dissolved linear polymer completely within the pores of the CPG, yet not be so much that removal of the excess solvent by vacuum evaporation would not be possible. In one embodiment, this is in the range of about 200 µM to about 600 µM of chloromethyl group/gram of CPG. In one embodiment, about 400 µM of chloromethyl group/gram of CPG is used in the invention. In this, example, where about 0.6 g of polyVBC is present, approximately 40 to 60 mls of DCM is present for every 10 g of CPG.

In one embodiment, crosslinking is performed by combining the cold CPG-polymer/monomer solution with the crosslinking agent. The crosslinking agent can be any compound having at least two functional groups that react with a reactive group of the monomeric subunit. For example, where the polymer is a poly(vinylbenzylchloride), the crosslinking agent can be any difunctional compound whose functional groups react with the benzyl chloride moiety of the vinylbenzylchloride (VBC) monomer. The functional groups at either end of the difunctional compound (crosslinker) can be different from each other or the same. Some examples of such functional groups include, but are not limited to, amines, thiols, diols, bisphenols, diphosphines, sulfonates, epoxides, nitriles, carboxylates, arylhalides, aldehydes, acetates, amides, carboxylic thioesters, phosphate esters and thioesters. In another embodiment, the polymer can be crosslinked using a Friedel-Crafts catalyst, including, but not limited to $AlCl_3$.

Suitably, the crosslinking reaction is performed in a manner which provides from about 2% to about 40% crosslinking, preferably about 5 to about 30% crosslinking (percentage of crosslinked vs non-crosslinked polymer based on total molar weight). In other embodiments, crosslinking is about 15%, about 20%, or about 25% (percentage of crosslinked vs non-crosslinked polymer based on total molar weight).

In one embodiment, the reaction mixture is maintained at a temperature below a value at which cross-linking will occur. This temperature is readily determined taking into consideration the selected crosslinking agent. In one embodiment, the temperature about 5° C., e.g., about 0 to about 5° C. prior to crosslinking. In one example, the crosslinking agent is diaminobutane (DAB). For convenience, the crosslinking agent (e.g., DAB) can be added as a solution. In one embodiment, the solvent is selected from among dichloromethane, tetrahydrofuran, 2-MeTHF, methyl ethyl ketone (MEK), ethyl acetate, benzene, butyraldehyde, chloroform and acetone, as described above.

The concentration of crosslinking agent in the solution can be adjusted depending upon the desired amount of crosslinking desired in the polymer coating. For example, where 0.6 g of polyVBC is used, and a 10% crosslinked polymer is the target, then 0.0352 g of 1,4 DAB should be added. If a 20% crosslinked polymer is desired, then 2× this amount, or 0.0705 g of 1,4 DAB should be used. In both cases, this amount of crosslinker is used for 0.6 g of polyVBC.

A second solvent is added to the mixture. In one embodiment, the second solvent has a boiling point higher than the reaction temperature for the crosslinking. Without wishing to be bound by theory, it is believed that this co-solvent remains behind, in the pores of the CPG during the crosslinking reaction done at the elevated temperatures. In one embodiment, the second solvent is a dichloroethane (DCE), e.g., 1,2-DCE. In yet another embodiment, the second solvent is 1,4-dioxane (also known as diethyleneoxide). Alternatively, 1,3-dioxane may be utilized.

The inventors have found that the loading numbers are significantly higher when the solvent is 1,4-dioxane. Without wishing to be bound by theory, the inventors believe that dioxane serves to keep a more "open" structure in the final polymer, which means more accessible functional groups (e.g., amine groups), and effectively a higher loading.

Typically, the crosslinking reaction is performed at a temperature of about 35° C. to about 65° C. For DAB, the crosslinking reaction is within this range, but is preferably above 38° C. The reaction is performed under a blanket of an inert gas, e.g., nitrogen. The reaction proceeds for at least about 12 hours up to about 24 hours, or longer.

Suitably, the first solvent is rapidly removed. Suitably, this solvent is removed within about 1 to about 1½ hours of addition of the crosslinking agent. At the desired completion of the crosslinking reaction, the CPG particles are cooled to room temperature. The resulting cooled, crosslinked polymer-coated CPG particles are then washed and dried using conventional organic chemistry techniques.

For example, coated CPG particles are washed in a suitable solvent, e.g., acetone, DCM, ethyl acetate, benzene, THF, butyraldehyde, chloroform, methyl ethyl ketone (MEK), benzene, butyraldehyde, acetone, and excess solvent removed. For example, the coated CPG particles can be dried under a stream of nitrogen or another inert gas. Alternatively, the excess solvent may be removed by vacuum evaporation (e.g., using a dessicator or rotovap).

The resulting polymer-coated controlled porosity glass (CPG) particle is crosslinked in the range of about 5 to about 30%. Desirably, the coated particle contains a conformal coating in at least a monolayer, where the coating has a thickness of about 20 to about 100 angstroms.

The coated CPG particle is available for loading, where the polymer contains suitable functional groups. Alternatively, the polymer-coated CPG particle is ready for conversion to a functionalized coating. The higher loading capacity of the coated CPG particle of the invention is due to the presence of a greater percentage of functional groups attached to the polymer as compared to the number of functional groups attached to a native CPG particle. The amount of groups that are accessible to further reaction can be calculated by one of skill in the art using known methods.

Suitably, the polymeric coating is provided with functional groups such as, e.g., aldehydes, amino groups, epoxy, halides, carboxylic acid, esters, or mixtures thereof. Methods of providing these functional groups to the polymeric material are known to those of skill in the art. In one embodiment, the invention provides a coated article having amino functional groups for use in oligonucleotide synthesis. Alternatively, other functional groups may be selected for binding of nucleosides, peptides or for other applications.

In addition to amino groups, other functional groups (e.g., aldehydes, epoxy, halides, carboxylic acid, esters, or mixtures) can be provided to the polymeric coating. Suitable methods are known and have been described in the literature.

See, e.g., Florencio Zaragoza Dorwald, "*Organic Synthesis on Solid Phase*", Wiley-VCH, Weinheim, FRG, 2000.

In one aspect, the invention provides a method for preparing a poly(phthalidimidomethylstyrene)-coated controlled porosity glass (CPG) particle. In one embodiment, poly(chloromethylstyrene)-coated CPG particle prepared according to the invention is mixed with and dimethylformamide (DMF) or 1,4 Dioxane. In one embodiment, the DMF is anhydrous. The mixture is then reacted with potassium phthalimide. At completion, excess DMF and unreacted potassium phthalimide is removed using methods known to those of skill in the art. For example, excess DMF and unreacted potassium phthalimide can be removed by adding fresh DMF, washing the coated CPG in DMF, followed by washing in methanol, washing in water, and a further wash in methanol. Other suitable wash methods can readily be utilized. The resulting poly(phthalidimidomethylstyrene)-coated CPG particle is dried.

In another aspect, the invention provides a method for preparing a poly(aminomethylstyrene)-coated controlled porosity glass (CPG) particle which is useful, for example, for nucleoside loading. In one embodiment, a poly(phthalidimidomethylstyrene)-coated CPG particle is mixed with a suitable inert solvent (e.g., ethanol) to form a slurry, to which hydrazine is added. In another embodiment, an aqueous methylamine in dioxane may be used. Suitable concentrations (e.g., about 40%) of methylamine and ratios of methylamine to dioxane (e.g., a 1:3 v/v ratio) at a temperature of about 55° C. may be used. The reaction mixture is then heated to reflux to afford poly(aminomethylstyrene)-coated CPG particles. Following cooling of the mixture containing coated CPG particles to room temperature, the coated CPG particles are washed to afford the poly(aminomethylstyrene)coated CPG.

Thus, the invention further provides a poly(aminomethylstyrene)-coated controlled porosity glass (CPG) particle having a significantly higher number of available amino functional groups, as compared to a native (uncoated) CPG particle.

It will be understood that this methodology is provided for purposes of illustration only and that the present invention is not limited to polystyrene-coated CPG particles with amino functional groups. One of skill in the art is familiar with the methods for providing functional groups other than amino groups (e.g., aldehydes, epoxy, halides, carboxylic acid, esters, or mixtures), and for functionalizing polymers other than polystyrene.

Advantageously, the polymer coated CPG particle of the invention has an increased loading capacity as compared to the uncoated CPG particle and increased stability as compared to a polystyrene-based particle, thereby supporting more synthetic chains. In one embodiment, a coated article according to the invention can have a loading capacity of at least 2 fold higher than its uncoated counterpart. For example, a coated article of the invention having an average pore diameter size of at least about 1000 Angstroms can be loaded with nucleoside in an amount of at least 100 μmoles per gram.

The coated particle of the invention is useful for synthesis of a variety of molecules including, e.g., oligonucleotides. Thus, in one aspect, the invention provides a coated particle having at least one ligand bound thereto. In one embodiment, the ligand is a nucleoside compound. Thus, the invention further provides a vessel for solid phase chemical synthesis which contains a plurality of coated particles of the invention.

In another embodiment, the invention provides a method for increasing the yield for solid phase synthesis of a ligand, which involves the use of a coated particle according to the present invention.

The following examples are illustrative of the invention and are not a limitation thereon.

EXAMPLES

The following Table shows the comparison of maximum loading achieved with the amine moiety coupled to the native glass (typical) and the amine moiety coupled through the polymer coated CPG of the invention.

| Comparison of Maximum Loading achieved with normal and polymer coated CPG | | | |
|---|---|---|---|
| CPG Type | Pore Size (Å) | Maximum Amine Load (μM/g) | Maximum Nucleoside Load (μM/g) |
| Amine on Native CPG | 1000 | 100 | 50 |
| poly(aminomethylstyrene) CPG Prepared Using 1,4-Dioxane | 1000 | 307 | 153 |
| poly(aminomethylstyrene) CPG Prepared Using DCE | 1000 | 224 μM/g | 82 μM/g |
| Amine on Native CPG | 1800 | 75 | 35 |
| poly(aminomethylstyrene) CPG Prepared Using 1,4-Dioxane | 1800 | 260 | 100 |

Example 1

Preparation of 20% Crosslinked Polyvinylbenzylchloride-Coated CPG Particles

A. Preparation of Solutions

Reagent quantities for two batches which were run are shown in the table.

| | CPG/20% Crosslinked Poly(VBC) | |
|---|---|---|
| | Amount | |
| Reagent | Batch 1 | Batch 2 |
| CPG (~1000 Angstroms) | 10 g | 25 g |
| DCM | 60 mL | 150 ml |
| Poly(VBC) | 0.61 g in 50 ml | 1.525 g in 125 ml |
| 1,4-diaminobutane (DAB) | 0.0705 g in 10 ml | 0.176 g in 25 ml |

A solution of Poly(VBC) in DCM is prepared at a concentration of 0.61 g poly(VBC) per 50 mL DCM.

A solution of 1,4-diaminobutane/DCM is prepared at a concentration of 0.0705 g DAB per 10 mL DCM.

Both mixtures are cooled to at least 0° C. in an ice bath.

B. Coating and Crosslinking of Poly-VBC

CPG (10 g/25 g) is added to a reaction flask, and then chilled to 0° C. Cold polyVBC (50 ml/125 ml) solution is added to the CPG and agitated at atmospheric pressure, 0° C. for 15 min. Cold DAB (10 ml/25 ml) is added to the flask. The mixture is agitated for at least 15 minutes at 0° C. DCM is removed from the flask by vacuum, keeping the mixture at 0° C. at all times. When enough DCM has been removed, the net weight of the CPG should be: 25.8 g (for 10 g batch) or 64.54 g (for 25 g batch)+/−10%.

This solvent removal process should be completed within an hour in order to avoid premature crosslinking of the polymer. The flask is placed under a static blanket of nitrogen and heated to 38° C. overnight to effect the crosslinking reaction of poly (VBC) to crosslinked polychloromethylstyrene. The flask is cooled, weighed, and placed in a stream of dry nitrogen until the net weight of the product is 10.68 g (10 g batch) or 26.7 g (25 g batch).

The coated polychloromethylstyrene CPG is washed in 10× acetone three times, and dried in a dessicator overnight.

C. Conversion of Poly(chloromethylstyrene) to poly(phthalimidomethylstyrene)

The poly(chloromethylstyrene) CPG is placed in a 1 liter Schott bottle to which 200 mls (10 g)/250 mls (25 g) of anhydrous DMF is added. The CPG/DMF mixture is purged with nitrogen for 15 minutes. 2.225 g (10 g)/2.8 g (25 g) of potassium phthalimide is added to the Schott bottle. The Schott bottle is agitated at 50° C. overnight. The poly(phthalimidomethylstyrene) CPG is washed 3× with fresh DMF (10×), followed by 2× in methanol (10×), 2× in water (10×) and a final 1× in methanol (10×), and dried in a dessicator overnight.

D. Conversion of poly(phthalimidomethylstyrene) to poly(aminomethylstyrene)

The coated CPG is transferred into a three neck 500 ml reaction flask to which anhydrous ethanol (200 mls (10 g)/250 mls (25 g)) is added. The CPG/EtOH slurry is placed in an oil bath, and an overhead stirrer fixed through the center port. 12.25 mls of anhydrous hydrazine is slowly added to the slurry, while stirring continuously. The EtOH mixture is refluxed overnight then cooled to room temperature while stirring continuously. The slurry is washed 1× with ethanol (10×), followed by 3 washes with acetone (10×) and dried in a vacuum dessicator overnight. Amine loading is determined by a non-aqueous colorimetric pH titration method.

Example 2

Preparation of CPG Coated with 15% Cross-Linked PolyvinylbenzylChloride (Poly(VBC)

A. Preparation of Solutions

Reagent quantities which were run are shown in the table.

| | CPG/15% Crosslinked Poly(VBC) | |
|---|---|---|
| | Amount | |
| Reagent | Batch 1 | Batch 2 |
| CPG | 10 g | 25 g |
| 1,2 Dichloroethane (DCE) or 1,4 Dioxane | 10 ml | 25 ml |
| Dichloromethane (DCM) | 60 mL | 150 ml |
| Poly(VBC) | 0.61 g in 50 ml | 1.525 g in 125 ml |
| 1,4 diaminobutane (DAB) | 0.053 g in 10 ml | 0.1325 g in 25 ml |

A solution of Poly(VBC) is prepared at a concentration of 0.61 g poly(VBC) per 50 mL DCM.

A solution of 1,4-diaminobutane/DCM is prepared at a concentration of 0.053 g DAB per 10 mL DCM.

Both mixtures, as well as the DCE or 1,4 dioxane, are cooled to 0° C. in an ice bath.

B. Coating and Cross-Linking of CPG

The coating and cross-linking of CPG is performed as described in Example 1, with exception that the cold DCE or 1,4-Dioxane is added to the cold polyVBC solution (which is rotated at atmospheric pressure, 0° C. for 5 min), prior to addition of the cold DAB. When DCM has been removed, (leaving only the DCE or the 1,4 dioxane), the targeted net weight of the CPG is 23.2 g (for 10 g batch) or 58 g (for 25 g batch)+/−10%. After the crosslinking reaction, and following the cooling of the flask the remaining DCE or 1,4 dioxane is removed by rotovap, until the net weight of the product=10.68 g (10 gram batch) or 26.7 g (25 g batch).

Poly(chloromethylstyrene) is converted to poly(phthalimidomethylstyrene) and poly(phthalimidomethylstyrene) is converted to poly(aminomethylstyrene) as described in Example 1.

C. Oligonucleotide Synthesis with CPG Coated with 15% Cross-Linked PolyvinylbenzylChloride (Poly(VBC) Support In order to assess the usefulness of the Poly(VBC) coated linked CPG support prepared as described in Example 2. More particularly, a 22-mer oligonucleotide sequence: SEQ ID NO: 1: CGC ACT TCA GGC TCC TGG GC(N)T, where N can be any nucleotide, was synthesized using the coated CPG hybrid support prepared as described in Example 2A and 2B in a 24 mL column, which was loaded at 80 μmole/gram. The oligonucleotide syntheses were performed using the standard protocols described in the AKTA 10 OligoPilot Operating Manual. For comparative purposes, a conventional 30% crosslinked conventional polystyrene support was used, with loading at 85 μmole/gram.

In the following table, FLP % refers to the yield of the full-length oligonucleotide product compared to theory; crude N−1% refers to failed sequences that are lacking only one nucleoside; coupling efficiency refers to the average nucleoside coupling efficiency over the entire synthesis. The polystyrene support is available from 3-Prime, LLC (Part number PS-DT-S-5).

The following table shows a single impurity, N−1 obtained in this synthesis. A similar assortment of other impurities was present for each synthesis, as determined by capillary electrophoresis chromatograms.

| | 30% Crosslinked Conventional Polystyrene (loaded @85 μmole/g) 24 mL Column | 2-Mer Oligonucleotide Sequence, SEQ ID NO: 1 CGC ACT TCA GGC TCC TGG GCNT | 15% Crosslinked Hybrid Support (loaded @80 μmole/g) 24 mL Column |
|---|---|---|---|
| Synthesis Scale | ~442 μmole | | ~640 μmole |
| Crude Recovery | 256.4 μmole | | 309.3 μmole |

-continued

|  | 30% Crosslinked Conventional Polystyrene (loaded @85 µmole/g) 24 mL Column | 2-Mer Oligonucleotide Sequence, SEQ ID NO: 1 CGC ACT TCA GGC TCC TGG GCNT | 15% Crosslinked Hybrid Support (loaded @80 µmole/g) 24 mL Column |
|---|---|---|---|
| % Recovery | 58.0% |  | 48.3% |
| Crude FLP% | 80.9% |  | 66.8% |
| Crude N-1% | 0.9% |  | 1.4% |
| Coup. Efficiency | 98.9% |  | 97.9% |

These results show that, even with the lower loading, the polymer coated CPG afforded a higher total amount of 22-mers synthesized (by weight) and a higher total amount of crude 22-mers recovered (by weight). Therefore, even though the recovery was slightly lower for the polymer coated CPG than the conventional support as a percentage, at least comparable amounts of 22-mers were recovered from the polymer coated CPG than the conventional support. Thus, the polymer coated CPG of the invention is advantageous in view of the fact that the polymer coated CPG of the invention was loaded at a lower concentration and at a lower percentage of crosslinking and thus, used less starting material. The difference between 80 µM/g and 85 µM/g is unimportant, since more of the polymer-coated support was used than the amount used in the PS case. This is indicated by the "synthesis scale" numbers which show 442 µMoles of starting nucleoside for the PS vs 640 µMoles of starting nucleoside for the polymer-coated support. Unfortunately, these results do not show any real advantage to using the polymer-coated CPG. However, it is not too much of a stretch to say that "comparable" results were obtained. What should be shown in future testing is that for a longer oligonucleotide synthesis (35-50 mer), the PS-coated support should give superior results. Another future test should be to load the reaction vessel with a maximum amount of solid support. The PS support will swell to several times it's volume, so far less can be used—thus limiting the maximum scale of synthesis for a given reactor volume.

Example 3

Preparation of Polymer Coated CPG Formed from Monomers

A. Removing Inhibitor from Monomer Solutions

The vinyl benzyl chloride, and divinylbenzene monomers are treated with activated alumina to remove the polymerization inhibitor present in the commercially purchased monomer solutions.

B. Adsorption of Monomer Mixture

Add 10 g of native CPG (pore diameter=~1000 Å) CPG to a reaction flask. Place the flask, with the dry CPG in the rotary evaporator and pull a vacuum for ~10 minutes while rotating the flask slowly. Release the vacuum by purging the system with nitrogen, and repeat this process 2 more times. Purge 100 mls of acetone with nitrogen for 15 minutes, while stirring at a moderate rate. Add the nitrogen purged acetone to the CPG while maintaining a blanket of nitrogen. Add 0.56 ml of the uninhibited vinyl benzyl chloride to the flask, while maintaining a nitrogen blanket. Add 0.052 ml of uninhibited divinyl benzene, while maintaining the nitrogen blanket. Add 0.0122 g of Benzoylperoxide (BPO) to the flask, still maintaining a nitrogen blanket. Slowly rotate the flask for about 10 minutes at atmospheric pressure. After 10 minutes, begin the rotary evaporation of the excess acetone, until the mixture achieves a net value of 19-21 g (~10 g of excess solvent)

C. Equilibration and Polymerization of the Monomer in the CPG Pores

Attach the flask and its contents to a vacuum pump, and pull a vacuum. Close the vacuum valve, then turn off the pump and allow the flask to sit in the bath at 50° C., for 24 hours, under a vacuum of 0.5-1 torr. Monitor the vacuum and re-evacuate as necessary (moderate vacuum only) if the pressure increases in the flask to maintain a vacuum. While maintaining a moderate static vacuum, heat the water or oil bath to 80° C. for 18-24 hours to effect the polymerization. Stirring or rotating is not necessary, but an oxygen free environment during this process is absolutely necessary. Allow the mixture to cool to room temperature. Evacuate any excess acetone in the reaction flask, to a final net weight of 10.77 g+1/−10%. Wash the polymer coated CPG (2×) with acetone (10×). Dry at 50° C., under vacuum, overnight Poly(chloromethylstyrene) is converted to poly(phthalimidomethylstyrene) and poly(phthalimidomethylstyrene) is converted to poly(aminomethylstyrene) as described in Examples 1 and 2.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

The invention claimed is:

1. A method for chemical synthesis of a molecule, said method comprising:
performing chemical synthesis utilizing a conformal polymer-coated controlled porosity glass (CPG) particle which comprises:
(a) a controlled porosity glass core having pores with a mean average diameter of 500 Angstroms to 4000 Angstroms (50 nm to 400 nm); and
(b) a conformal cross-linked polymeric coating over said core, wherein said polymer comprises a cross-linking agent and monomeric subunits or a polymerizable monomer selected from the group consisting of a vinylbenzylchloride, an acrylic, a styrene, and mixtures thereof,
wherein the conformal polymeric coating layer is on the surface of the CPG particle and within its pores without changing the shape of the uncoated CPG particle, said polymeric coating layer comprising one or more functional groups capable of binding a ligand which is a point of attachment to the molecule to be synthesized, said one or more functional groups selected from the group consisting of one or more of an aldehyde, amino group, epoxy group, halide, carboxylic acid, ester, and mixtures thereof.

2. The method according to claim 1, wherein the synthesis is performed in a vessel comprising a plurality of the conformal polymer-coated CPG particles.

3. The method according to claim 1, wherein the functional group comprises amino groups for oligonucleotide synthesis.

4. The method according to claim 1, wherein the ligand comprises a nucleoside.

5. The method according to claim 1, wherein the pores within the conformal coated CPG particle retain an average pore size of at least 90% of the average pore size of the uncoated CPG particles (a), based on dry pore size.

6. The method according to claim 1, wherein the polymeric coating adheres to the CPG core is the absence of a coupling agent to link the coating to the CPG particle.

7. The method according to claim 1, wherein the polymeric coating is crosslinked in an amount of about 5% to about 30% crosslinked polymer versus non-crosslinked polymer based on total molar weight of the polymeric coating.

8. The method according to claim 1, wherein coating comprises a polystyrene polymer, a methyl methacrylate polymer, or mixtures thereof.

9. The method according to claim 5, wherein the coating comprises a polystyrene polymer.

10. The method according to claim 1, wherein the crosslinking agent comprises a diaminobutane.

11. The method according to claim 1, wherein said coating comprises a thickness of about 20 to 100 Angstroms.

12. The method according to claim 10, wherein said coated particle contains pores with a mean average diameter of 500 to 3000 Angstroms.

13. The method according to claim 10, wherein said coated particle contains pores with a mean average diameter of 500 to 2000 Angstroms.

14. The method according to claim 1, wherein said coating comprises about 5% w/w to about 25% w/w of the total weight of the coated particle.

15. The method according to claim 14, wherein said coating comprises about 5% w/w to about 10% w/w of the total weight of the coated particle.

16. The method according to claim 1, wherein said coated particle has a mean average pore diameter size of at least about 1000 Angstroms and is loaded with nucleoside in an amount of at least 100 μmoles per gram.

17. The method according to claim 1, wherein said ligand is a nucleoside compound.

18. A method for solid phase synthesis comprising synthesizing nucleosides on a conformal polymer-coated controlled porosity glass (CPG) particle comprising:
(a) a controlled porosity glass core having pores with a mean average diameter of 500 Angstroms to 4000 Angstroms (50 nm to 400 nm); and
(b) a conformal cross-linked polymeric coating comprising one or more amino functional groups over said core, wherein said polymer further comprises a cross-linking agent and monomeric subunits or a polymerizable monomer selected from the group consisting of a vinylbenzylchloride, an acrylic, a styrene, and mixtures thereof,
wherein the conformal polymeric coating layer is on the surface of the CPG particle and within its pores without changing the shape of the uncoated CPG particle, said one or more amino functional groups providing a point of attachment to the nucleosides.

* * * * *

SEQUENCE LISTING

<160> NUMBER OF SEQ ID NOS: 1

<210> SEQ ID NO 1
<211> LENGTH: 22
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (21)..(21)
<223> OTHER INFORMATION: can be any nucleotide

<400> SEQUENCE: 1
cgcacttcag gctcctgggc nt                                           22